United States Patent [19]
Pardini

[11] Patent Number: 5,874,065
[45] Date of Patent: Feb. 23, 1999

[54] ORAL ANTI-ACID PASTE AND METHODS OF USE

[76] Inventor: Alan A. Pardini, 2344 Palo Danzante, Alpine, Calif. 91901

[21] Appl. No.: 882,850

[22] Filed: Jun. 26, 1997

[51] Int. Cl.⁶ .............................. A61K 7/16; A61K 7/18; A61K 33/06; A61K 33/16

[52] U.S. Cl. ........................... 424/498; 424/52; 424/673; 424/676; 424/684; 424/685; 424/686; 424/687; 424/688; 424/689; 424/690; 424/691; 424/692; 424/693

[58] Field of Search ....................... 424/49–52, 673–676, 424/684–693

[56] References Cited

U.S. PATENT DOCUMENTS

| | | | |
|---|---|---|---|
| 152,098 | 6/1874 | Forster | 167/93 |
| 926,280 | 6/1909 | Morrison, I | 167/93 |
| 947,120 | 1/1910 | Morrison, II | 167/93 |
| 1,536,305 | 5/1925 | Nitardy, I | 167/93 |
| 1,591,727 | 7/1926 | Nitardy, II | 167/93 |
| 1,622,391 | 3/1927 | Nitardy, III | 167/93 |
| 1,817,664 | 8/1931 | Badanes | 167/93 |
| 2,089,845 | 8/1937 | Atkins | 167/93 |
| 2,550,207 | 4/1951 | Tainer | 167/93 |
| 2,818,371 | 12/1957 | Wessinger | 167/93 |
| 2,843,521 | 7/1958 | Entrekin | 167/56 |
| 3,119,743 | 1/1964 | Ericksson | 167/93 |
| 3,703,578 | 11/1972 | Cella, I | 424/49 |
| 3,864,471 | 2/1975 | King et al. | 424/52 |
| 3,885,028 | 5/1975 | Cella, II et al. | 424/52 |
| 3,980,767 | 9/1976 | Chow et al. | 424/52 |

*Primary Examiner*—Shep K. Rose
*Attorney, Agent, or Firm*—Thomas Fitting

[57] ABSTRACT

The invention describes an oral anti-acid paste comprising anti-acid compound in a slow releasing carrier medium which disperses the anti-acid, and releases the anti-acid from the paste upon contact with the aqueous media such as saliva. The paste can be used by placement in the mouth for slow release of the anti-acid into the saliva thereby contacting the mucosa of the esophagus to inhibit irritation to the mucosa due to excess acid.

20 Claims, No Drawings

ORAL ANTI-ACID PASTE AND METHODS OF USE

TECHNICAL FIELD

This invention relates to an oral anti-acid paste for protection of the stomach and esophagus from the reflux of stomach acid causing the condition commonly known as "heartburn".

BACKGROUND OF THE INVENTION

The aim of the traditional anti-acid is to coat the sensitive tissues and neutralize acid within the stomach. Attempts have been made to protect the sensitive esophageal tissues from the effect of stomach acids which is sometimes allowed to reflux up and out of the stomach, into the esophagus. The acid damages this sensitive tissue, causing scarring and constriction which can lead to difficulty in swallowing. The common time during which this reflux occurs is in bed, when the patient is lying down, and the effect of gravity aids the acid in its exit from the stomach.

Traditional anti-acid liquids simply drain down into the stomach, leaving the esophagus unprotected. Other forms of medication attempt to inhibit the creation of acid by administration of biochemical modulators. This is only partially effective and the medication is expensive and not free of side effects. There is another form of anti-acid which in theory is designed to bubble up, and is referred to as a "foam tab". This design is ineffective at protecting the esophagus, and is no better than the liquid or pill form of chewable anti-acids, in that it is confined to the stomach, and its effects and benefits are limited to the stomach.

BRIEF SUMMARY OF THE INVENTION

It has now been discovered that an oral, semi-solid paste containing anti-acid base compounds formulated according to the present invention blocks the effect of acid on the soft tissues of the esophagus and stomach by gradually releasing ant-acid, such as calcium carbonate, slowly and continually, over the tissues. The advantage of the invention is its ability to provide constant protection to the mucosa of the esophagus as well as the stomach, during the time that the tissues are at the greatest risk, i.e., during the hours of sleep, when the horizontal posture allows the reflux of stomach acid up into the esophagus. The paste consistency allows the anti-acid to remain in the mouth where it is slowly dissolved, providing sustained protection and pain relief.

In preferred embodiments the anti-acid compound is calcium carbonate. This anti-acid provides a benefit to the patient from the calcium contained in the paste. Calcium carbonate is the best dietary source of additional calcium for the prevention of osteoporosis, and is often prescribed for this purpose.

In another preferred embodiment, mineral oil or other dietary lubricant is used in the formulation of the paste. The lubricant, which upon admixture with the base converts powdered calcium carbonate into a paste, serves as a lubricant to the bowel, and is often prescribed to prevent constipation.

Other advantages and embodiments will be apparent to one skilled in the art of the invention.

DETAILED DESCRIPTION OF THE INVENTION

An oral anti-acid paste of the present invention is a thick and malleable paste, containing anti-acid in a slow release formulation. The paste is used as a means for delivery of anti-acid base compound to the oral passages in patients in which excess acid produces medical conditions.

An important and novel feature of the paste is consistency which allows it to be formed in a variety of shapes. The ideal consistency is a semi-solid, which can be molded to conform with the anatomy of the mouth by the pressure of the tissues of the mouth.

The consistency of the paste is such that it is sticky and malleable enough to conform with the anatomy of the mouth which prevents it from being dislodged and swallowed as a solid. The paste is preferably formed into a strip which can be pinched off into lengths of approximately two centimeters (cm), and placed into the mouth, between the cheek and the gums or teeth. The saliva immediately begins to dissolve the paste and release a stream of the chemical into the esophagus, which is swallowed unconsciously, just as the saliva is swallowed.

The paste works by continually and slowly being dissolved by the inherent production of the saliva by the human salivary glands. The resulting mixture of anti-acid with saliva creates a liquid which is released and drains slowly, over the hours of use, down the throat and over the tissues of the esophagus and stomach. This effectively neutralizes and protects the sensitive tissues, avoiding the pain response which is familiar as "heartburn".

The paste is particularly suited for use during sleep because the consistency allows the paste to remain stationary without discomfort and provides prolonged release of anti-acid.

When used during sleep, the slow release of ant-acid is particularly useful because the protective properties of anti-acid are prolonged and utilized during a time when the patient is unconscious, but at greatest risk of damage to the effects of acid on the unprotected and delicate esophageal tissues. In the short term, this leads to loss of sleep due to pain. It can mimic the discomfort of a myocardial infarction, or "heart attack", obviously leading to expense and anxiety in terms of medical evaluation and hospitalization. The long term effect of this acid reflux on the tissues of the esophagus causes scarring of the esophagus and the formation of constricting bands which can lead to food becoming caught in the esophagus. This is a relatively common emergency, and requires a general anesthetic and removal of the food obstruction by a specialist. The continual irritation of unbuffered acid is thought to provide an environment for the creation of peptic ulcers within the stomach and esophagus. Peptic ulcers, over the years, are thought to be precursors of gastric carcinoma.

A. Oral Anti-Acid Paste

The anti-acid oral paste of the present invention is a formulation suited for slow release of an anti-acid base compound and has a malleable consistency as described herein. The paste can contain any of a variety anti-acid base compounds present in the unique consistency of the invention.

The consistency of a paste of this invention is that which allows malleable plasticity of a semi-solid. Preferably, the paste is soft enough to provide comfort when in the mouth such that the patient can sleep and be unaware of the presence of the paste. The plasticity encourages the paste to remain stationary where placed between the cheek and gums, so that the patient does not swallow the semi-solid paste whole.

The paste is further formulated to allow for slow dissolution of the anti-acid base and other constituents of the paste, and to dissolve with the saliva that is produced in the mouth as a normal function. If asleep, the patient can swallow the dissolved paste material unconsciously during sleep.

The paste is typically formed by mixing a dry powder form of base compound with a liquid that will not evaporate. Preferably, the liquid can act as a diatetic lubricant.

1. Anti-Acid Compounds

Anti-acid compounds suitable for use in the present paste can be any of a variety of basic (acid-neutralizing) compounds (anti-acids) which are typically formulated into a physiologically tolerable base composition. An anti-acid composition typically contains base, preferably an aqueous base, and may further contain buffers and salts.

A basic compound suitable for use typically has mild basicity and is any substance which dissociates on solution in water (i.e., an aqueous base) to produce one or more hydroxyl ions, or more generally is any substance which has can accept a proton, or which has an unshared pair of electrons.

Typical basic compounds suitable for the present invention include carbonates, bicarbonates, chlorides, hydroxides, dibasic citrates phosphates, sulfates and the like, typically in the form of a salt. Typical salts include a complex with sodium, potassium, calcium, ammonium, aluminum, magnesium, and the like.

Preferred basic compounds include sodium carbonate, potassium carbonate, calcium carbonate, ammonium bicarbonate, ammonium carbonate, ammonium chloride, ammonium hydroxide, dibasic ammonium citrate, ammonium phosphate (monobasic or dibasic), ammonium sulfate, aluminum carbonate, aluminum hydroxide, calcium citrate, calcium hydroxide, magnesium carbonate, magnesium hydroxide, magnesium phosphate (dibasic), potassium hydroxide, potassium bicarbonate, and the like.

Particularly preferred are the basic compounds aluminum carbonate, aluminum hydroxide and calcium carbonate. In one embodiment, a basic composition can be present in the form of mixtures of basic compounds, such as aluminum hydroxide and aluminum carbonate.

An oral anti-acid paste contains a basic compound in a amount sufficient to provide detectable acid neutralization. A preferred paste contains sufficient base to provide from about 0.01 to 1 acid-neutralizing equivalents of a paste containing 0.4 grams (gm) calcium carbonate per gram of paste. A preferred paste contains an amount of base sufficient to provide an acid-neutralizing equivalent of about 0.02 to 0.4 gm, preferably about 0.1 to 0.2 gm, of calcium carbonate per gm paste.

An acid-neutralizing equivalent is an amount of a basic compound that can neutralize an equal (equivalent) amount of acid as can be neutralized by the specified base in an acid neutralization assay. Acid neutralization assays are fundamental to chemistry, and any suitable assay can be used. Typical assays involve titration of acid with base in the presence of pH indicators.

A preferred paste contains from about 38 to 75% weight of powdered calcium carbonate per volume (w/v) paste.

2. Slow Releasing Carrier Medium

The anti-acid paste can contain any of a variety of materials suitable as a carrier which provide a semi-solid consistency and facilitate slow release of the basic compounds in the paste. Preferred materials are partially resistant to dissolution in aqueous solutions such as saliva. Preferred materials are immiscible or substantially immiscible with water, such as oils, alcohols, gels or polymers such as cellulose. Preferred oils include mineral and vegetable oils. Particularly preferred is mineral oil. Preferred alcohols are glycerin and glycerol. Preferred cellulose polymers are hydroxycellulose and hydroxyethylcellulose.

The paste may also contain gelatinous materials to assist in the consistency. Preferred gels are fluoride gels, such as stannous fluoride. A typical paste contains from about 0.1 to 75% weight stannous fluoride per weight paste, and a preferred paste contains about 0.4% w/w.

A slow releasing carrier medium releases ant-acid over time. A typical medium releases approximately 90% of its anti-acid in about 1 to 24 hours, and preferably from about 2 to 12 hours. In actual use, the rate of release will be affected by the amount of saliva produced by the patient, and the degree of mouth agitation that contributes to mixing the saliva with the paste. However, under control circumstances, such as suspension of the paste in a physiological solution of physiologic pH, salt, osmolarity, etc., one can readily determine rates of anti-acid release. A typical controlled release system involves a strip of paste, such as is prepared in Example 1, formed into a one-inch strip that is ½ inch wide and ⅛ inch thick, and normal saline buffered at pH 7.0 with 10 mM phosphate.

Formulations that provide slow release can vary to suit different patient's needs. For example, the composition can be formulated for very slow release, typically 90% release at 24 hours, for patients who excessively agitate the paste, or for patients with a mild reflux condition. Alternatively, the composition can be formulated for rapid release, typically 90% release at 1 to 6 h, or as needed, for patients with severe reflux conditions.

Exemplary formulations are described herein.

3. Semi-Solid Consistency

A paste of the present invention is formulated to provide a malleable, semi-solid consistency. The paste is preferably the consistency of a gum that can be easily molded into the contours of the mouth.

An exemplary paste has the consistency of a paste that contains from 3 to 9 mls stannous fluoride per 16 gms dry, powdered calcium carbonate. A particularly preferred paste has the consistency of a paste that is prepared using 6 ml Gel-Kam Home Care Gel (stannous fluoride gel; Colgate Oral Pharmaceuticals, Inc.) and 16 gms dry calcium carbonate.

B. Therapeutic Methods and Compositions

An anti-acid paste of the present invention is a therapeutic composition formulated to ameliorate any of a variety of medical conditions in which excess acid plays a role. The paste contains a therapeutically effective amount of an anti-acid base compound. An effective amount is a predetermined amount calculated to achieve the desired effect, i.e., an amount sufficient to release acid-neutralizing anti-acid and produce the desired result, and can vary widely depending upon the particular disease condition to be treated, the potency of the anti-acid compound and the release rate formulated into the paste. Thus, an effective amount can be measured by improvements in one or more symptoms associated with the excess acid condition occurring in the patient. Typically, an effective amount is an amount sufficient to provide detectable acid neutralization, and more preferably is an amount described herein for an oral anti-acid paste of the invention.

Thus, the dosage ranges for the administration of an anti-acid compound in a paste composition of the invention are those large enough to produce the desired effect in which the condition of excess acid to be treated is ameliorated. The dosage should not be so large as to cause adverse side effects. Generally, the dosage will vary with the age, condition, sex and extent of the disease in the patient and can be determined by one of skill in the art. The dosage can be adjusted by the individual physician in the event of any complication.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for oral application are disclosed herein and depend on the conditions of administration. Suitable regimes for administration are also variable, but are typified by an initial administration followed by repeated doses at one or more intervals by a subsequent administration of the paste.

Insofar as an oral anti-acid paste is used therapeutically, the paste itself is a therapeutic composition and as such may also contain additional components. For example, the paste may contain flavorings, fillers, preservatives, supplements, additional medicaments, and the like components.

Typical flavorings include any of a variety of known flavorings, such as food flavorings, particularly mints such as spearmint or peppermint, and sweeteners. Food flavorings can be obtained from a variety of commercial sources, such as imitation flavoring extracts (Durkee). Sweeteners can include natural or artificial sweeteners, including but not limited to sucrose, glucose, fructose, corn starch, glycerol, aspartame, saccharin, and the like sweeteners. Flavorings can be added for taste, as is well known.

The use of preservatives is well known, and any of a variety of preservatives can be used. Exemplary preservatives include magnesium stearate, stearic acid, microcrystallilne cellulose, crosscarmellose sodium maltodextrin, glycerin, hydroxyethylcellulose.

Additional medicaments for use in a paste of the present invention can include fluoride, particularly fluoride gel, preferably 0.4% (w/w) fluoride. Additional supplements can include dietary supplements such as vitamins, minerals and the like. A particularly preferred supplement is calcium.

A therapeutic paste of this invention can contain a physiologically tolerable carrier together with at least one species of anti-acid compound, dispersed therein as an active ingredient.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal or human without the production of undesirable physiological effects such as nausea, dizziness, gastric upset and the like.

The preparation of a pharmacological composition that contains active ingredients dispersed therein is well understood in the art. Typically such compositions are prepared as sterile compositions either as liquid solutions or suspensions, aqueous or non-aqueous, however, suspensions in liquid prior to use can also be prepared.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the base addition salts that are formed with inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions such as water, or that contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water, such as oils or alcohols. Exemplary of such additional liquid phases are glycerin, mineral oils, vegetable oils such as cottonseed oil, organic esters such as ethyl oleate, and water-oil emulsions.

In one embodiment, the invention also contemplates a method for reducing the irritant effects of excess acid in the mouth, throat, esophagus, stomach and related digestive system tissues comprising administering an oral anti-acid paste according to the present invention.

In a related embodiment, the method is suitable for reducing acid in the esophagus or stomach of a patient susceptible to acid refluxitis during resting periods. The method comprises maintaining an oral anti-acid paste according to this invention in the mouth during the resting period. The paste is placed and maintained in the mouth between the teeth and cheek or between the teeth and lips during the resting period. Typically, a resting period is from about 30 minutes to 12 hours, and can vary as is normal for resting periods.

The method can be practiced on a variety of mammals, including agricultural stock such as cow, sheep, horse, goat, pig, and the like, pets such as cats, dogs or other domesticated mammals, and particularly humans.

In one embodiment, the administration of an oral anti-acid paste can be repeated at defined intervals to provide prolonged acid neutralization and effectiveness.

C. Formulations and Packaging

A variety of formulations can be prepared for use in an oral anti-acid paste of the present invention. Exemplary formulations are described in the Examples.

An exemplary and preferred formulation includes from 38 to 75% dry powdered calcium carbonate, expressed in percent weight per volume (w/v) paste, and from 25 to 62% (w/v) stannous fluoride. One exemplary formulation comprises about 70% w/v calcium carbonate and 30% w/v stannous fluoride.

An oral anti-acid paste of the present invention can be formulated into a variety of shapes, amounts and containers. This can include a package that contains, in an amount sufficient for at least one therapeutic treatment, one or more dosages of the paste, as a separately packaged reagent. Instructions for use of the packaged paste are also typically included.

"Instructions for use" typically include a tangible expression describing the anti-acid compound-containing paste and a parameter such as the relative amounts of anti-acid or carrier.

The term "package" refers to a solid matrix or material such as film, plastic, paper, foil and the like capable of holding within fixed limits an oral anti-acid paste of the present invention. Thus, for example, a package can be a foil wrapping used to contain a unit dosage of paste, or it can be a plastic dispenser containing the paste fashioned into a continuous tape in which the dosage is a function of the length of tape utilized.

EXAMPLES

The following examples are intended to illustrate but are not to be construed as limiting of the specification and claims in any way.
1. Formulation A
    6 ml stannous fluoride gel (Gel-Kam)
    16 gms powdered calcium carbonate
2. Formulation B
    6 ml stannous fluoride gel (Gel-Kam)
    15 gms powdered calcium carbonate
    0.2–0.8 ml imitation flavoring extract, peppermint, (Durkee)
3. Formulation C
    6 ml stannous fluoride gel (Gel-Kam)
    16 gms powdered calcium carbonate
    1–3 ml liquid glycerol
4. Patient Trials An anti-acid paste formulation was prepared as described in Example 1. The paste was provided to patients for self-administration by placing the paste in the mouth between the lips and gums, typically in amounts of about 2 to 5 cubic centimeters. All patients presented a condition of reflux-related esophageal irritation, pain or discomfort. After use, the patients were asked to rate the effectiveness of the paste in assisting symptoms of reflux.

Five patients used the paste to relieve night-time symptoms of reflux. Two patients reported 80% effectiveness, one patient reported 70% effectiveness and one patient reported 90% effectiveness of relief.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A method for reducing acid in the esophagus or stomach of a patient susceptible to acid refluxitis during resting periods comprising maintaining an oral anti-acid paste in the mouth during said resting period, wherein said oral anti-acid paste comprises a therapeutically effective amount of an ant-acid and a physiologically tolerable slow-releasing carrier medium capable of dispersing said anti-acid in said paste, wherein said paste has a semi-solid consistency.

2. The method of claim 1 wherein said anti-acid is an aqueous base selected from the group consisting of carbonate and hydroxide, and salts thereof.

3. The method of claim 2 wherein said carbonate base is calcium carbonate.

4. The method of claim 1 wherein said base is present in an amount sufficient to provide an acid-neutralizing equivalent of about 0.02 to 0.4 gm of calcium carbonate per gram of paste.

5. The method of claim 4 wherein said base is present in an amount sufficient to provide an acid-neutralizing equivalent of about 0.1 to 0.2 gm of calcium carbonate per gram of paste.

6. The method of claim 2 wherein said hydroxide base is selected from the group consisting of magnesium hydroxide and aluminum hydroxide.

7. The method of claim 1 wherein said carrier medium includes a buffered aqueous liquid, an oil or an alcohol.

8. The method of claim 1 wherein said carrier medium includes mineral oil, hydroxycellulose, hydroxyethylcellulose, glycerin or glycerol.

9. The method of claim 1 wherein said carrier includes fluoride gel.

10. The method of claim 1 wherein said fluoride gel contains stannous fluoride.

11. The method of claim 10 wherein said stannous fluoride is present in said paste at about 0.1 to 0.5% w/w.

12. The method of claim 1 wherein said stannous fluoride is present in said paste at about 0.4% w/w.

13. The method of claim 1 wherein said anti-acid is calcium carbonate and said carrier includes stannous fluoride.

14. The method of claim 10 wherein said calcium carbonate is from 38 to 75% weight per volume paste and said stannous fluoride is from 25 to 62% weight per volume paste.

15. The method of claim 10 having about 70% calcium carbonate (w/v) and about 30% stannous fluoride (w/v).

16. The method of claim 1 wherein said semi-solid consistency is between the consistency of a paste consisting of 3 mls stannous fluoride gel per 16 grams dry calcium carbonate and a paste consisting of 9 mls stannous fluoride gel per 16 grams dry calcium carbonate.

17. The method of claim 1 wherein said semi-solid consistency is the consistency of a paste consisting of 6 mls stannous fluoride gel and 16 grams dry calcium carbonate.

18. The method of claim 1 wherein said paste is maintained in the mouth between the teeth and cheek during said resting period.

19. The method of claim 1 wherein said paste is maintained in the mouth between the lips and teeth during said resting period.

20. The method of claim 1 wherein said resting period is from 30 minutes to 12 hours.

* * * * *